(12) United States Patent
Roose et al.

(10) Patent No.: US 8,808,302 B2
(45) Date of Patent: Aug. 19, 2014

(54) CUSTOMIZED PATIENT-SPECIFIC ACETABULAR ORTHOPAEDIC SURGICAL INSTRUMENT AND METHOD OF USE AND FABRICATION

(75) Inventors: Jeffrey R. Roose, Milford, IN (US); Jason T. Sherman, Warsaw, IN (US); Bryan Rose, South Whitley, IN (US); Anthony Metzinger, Warsaw, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 533 days.

(21) Appl. No.: 12/855,363

(22) Filed: Aug. 12, 2010

(65) Prior Publication Data

US 2012/0041445 A1    Feb. 16, 2012

(51) Int. Cl.
*A61B 17/56* (2006.01)
(52) U.S. Cl.
USPC ............................................................ 606/96
(58) Field of Classification Search
USPC .......................... 606/86 R, 87–89, 91, 96–99
See application file for complete search history.

(56) References Cited

U.S. PATENT DOCUMENTS

| | | |
|---|---|---|
| 3,698,017 A | 10/1972 | Scales et al. |
| 3,840,904 A | 10/1974 | Tronzo |
| 3,903,549 A | 9/1975 | Deyerle et al. |
| 4,475,549 A | 10/1984 | Oh et al. |
| 4,632,111 A | 12/1986 | Roche et al. |
| 4,711,233 A | 12/1987 | Brown |
| 4,715,860 A | 12/1987 | Amstutz et al. |
| 4,800,874 A | 1/1989 | David et al. |
| 5,007,936 A | 4/1991 | Woolson et al. |
| 5,098,437 A | 3/1992 | Kashuba et al. |
| 5,108,401 A | 4/1992 | Insall et al. |
| 5,133,660 A | 7/1992 | Fenick |
| 5,171,243 A | 12/1992 | Kashuba et al. |
| 5,320,529 A | 6/1994 | Pompa |
| 5,320,625 A | 6/1994 | Bertin et al. |
| 5,658,294 A | 8/1997 | Sederholm et al. |
| 5,768,134 A | 6/1998 | Swaelens et al. |
| 5,817,097 A | 10/1998 | Howard et al. |
| 5,824,085 A | 10/1998 | Sahay et al. |
| 5,942,370 A | 8/1999 | Neckers et al. |
| 5,976,149 A | 11/1999 | Masini et al. |
| 6,161,080 A | 12/2000 | Aouni-Ateshian et al. |
| 6,228,121 B1 | 5/2001 | Khalili |
| 6,264,698 B1 | 7/2001 | Lawes et al. |

(Continued)

FOREIGN PATENT DOCUMENTS

| | | |
|---|---|---|
| CA | 2501041 A1 | 4/2004 |
| CA | 2505371 A1 | 5/2004 |

(Continued)

OTHER PUBLICATIONS

Radermacher et al., "Computer Assisted Orthopaedic Surgery with Image Based Individual Templates", Clin Orthopaedics and Related Research 354, 28-38, 1998, 11 pages.

(Continued)

*Primary Examiner* — Christopher Beccia
(74) *Attorney, Agent, or Firm* — Barnes & Thornburg LLP

(57) ABSTRACT

A customized patient-specific acetabular orthopaedic surgical instrument is disclosed. A method for fabricating and using the orthopaedic surgical instrument us also disclosed.

16 Claims, 7 Drawing Sheets

(56) References Cited

U.S. PATENT DOCUMENTS

| | | |
|---|---|---|
| 6,273,891 B1 | 8/2001 | Masini |
| 6,327,491 B1 | 12/2001 | Franklin et al. |
| 6,344,043 B1 | 2/2002 | Pappas |
| 6,395,005 B1 | 5/2002 | Lovell |
| 6,427,698 B1 | 8/2002 | Yoon |
| 6,463,351 B1 | 10/2002 | Clynch |
| 6,738,657 B1 | 5/2004 | Franklin et al. |
| 6,944,518 B2 | 9/2005 | Roose |
| 6,953,480 B2 | 10/2005 | Mears et al. |
| 6,991,655 B2 | 1/2006 | Iversen |
| 7,534,263 B2 | 5/2009 | Burdulis, Jr. et al. |
| 7,559,931 B2 | 7/2009 | Stone |
| 7,618,451 B2 | 11/2009 | Berez et al. |
| 7,634,119 B2 | 12/2009 | Tsougarakis et al. |
| 7,651,501 B2 | 1/2010 | Penenberg et al. |
| 7,717,956 B2 | 5/2010 | Lang |
| 7,796,791 B2 | 9/2010 | Tsougarakis et al. |
| 7,824,181 B2 | 11/2010 | Sers |
| 7,981,158 B2 | 7/2011 | Fitz et al. |
| 8,133,234 B2 * | 3/2012 | Meridew et al. ............... 606/91 |
| 8,175,683 B2 * | 5/2012 | Roose ...................... 600/427 |
| 2002/0007294 A1 | 1/2002 | Bradbury et al. |
| 2004/0204760 A1 | 10/2004 | Fitz et al. |
| 2004/0236424 A1 | 11/2004 | Berez et al. |
| 2005/0107799 A1 | 5/2005 | Graf et al. |
| 2005/0148843 A1 | 7/2005 | Roose |
| 2005/0234461 A1 | 10/2005 | Burdulis et al. |
| 2005/0267584 A1 | 12/2005 | Burdulis et al. |
| 2006/0129160 A1 | 6/2006 | Liu et al. |
| 2007/0106305 A1 | 5/2007 | Kao et al. |
| 2007/0198022 A1 | 8/2007 | Lang et al. |
| 2007/0276400 A1 | 11/2007 | Moore et al. |
| 2008/0114370 A1 | 5/2008 | Schoenefeld |
| 2008/0147072 A1 | 6/2008 | Park et al. |
| 2008/0161815 A1 | 7/2008 | Schoenefeld et al. |
| 2008/0234665 A1 | 9/2008 | Godara et al. |
| 2008/0234685 A1 | 9/2008 | Gjerde |
| 2008/0243127 A1 | 10/2008 | Lang et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0306558 A1 | 12/2008 | Hakki |
| 2009/0088674 A1 | 4/2009 | Caillouette et al. |
| 2009/0131941 A1 | 5/2009 | Park et al. |
| 2009/0138020 A1 | 5/2009 | Park et al. |
| 2009/0149977 A1 | 6/2009 | Schendel |
| 2009/0163922 A1 * | 6/2009 | Meridew et al. ............... 606/88 |
| 2009/0222014 A1 | 9/2009 | Bojarski et al. |
| 2009/0270868 A1 | 10/2009 | Park et al. |
| 2009/0307893 A1 | 12/2009 | Burdulis, Jr. et al. |
| 2010/0016984 A1 | 1/2010 | Trabish |
| 2010/0023015 A1 | 1/2010 | Park |
| 2010/0042105 A1 | 2/2010 | Park et al. |
| 2010/0082035 A1 | 4/2010 | Keefer |
| 2010/0087829 A1 | 4/2010 | Metzger et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0191244 A1 | 7/2010 | White et al. |
| 2010/0212138 A1 | 8/2010 | Carroll et al. |
| 2010/0217338 A1 | 8/2010 | Carroll et al. |
| 2010/0274253 A1 | 10/2010 | Ure |
| 2011/0015639 A1 | 1/2011 | Metzger et al. |

FOREIGN PATENT DOCUMENTS

| | | |
|---|---|---|
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 2830566 A1 | 1/1980 |
| DE | 4219939 A1 | 12/1993 |
| EP | 645984 A1 | 4/1995 |
| EP | 756735 | 2/1997 |
| EP | 1486900 A1 | 12/2004 |
| EP | 1669033 A1 | 6/2006 |
| GB | 2426200 A | 11/2006 |
| KR | 2005072500 A | 7/2005 |
| KR | 2005084024 A | 8/2005 |
| TW | I231755 B | 5/2005 |
| WO | 9325157 A1 | 12/1993 |
| WO | 9528688 A1 | 10/1995 |
| WO | 0184479 A1 | 11/2001 |
| WO | 2005027755 A1 | 3/2005 |
| WO | 2004049981 A3 | 4/2005 |
| WO | 2005051239 A1 | 6/2005 |
| WO | 2005051240 A1 | 6/2005 |
| WO | 2005084558 A1 | 9/2005 |
| WO | 2006058057 A2 | 6/2006 |
| WO | 2006060795 A1 | 6/2006 |
| WO | 2007041375 A2 | 4/2007 |
| WO | 2007092841 A2 | 8/2007 |
| WO | 2007097854 A2 | 8/2007 |
| WO | 2007145937 A2 | 12/2007 |
| WO | 2008014618 A1 | 2/2008 |
| WO | 2008021494 A2 | 2/2008 |
| WO | 2008112996 A1 | 9/2008 |
| WO | 2009001083 A1 | 12/2008 |
| WO | 2009045960 A1 | 4/2009 |
| WO | 2009111512 A2 | 9/2009 |

OTHER PUBLICATIONS

Hafez et al., "Computer-assisted Total Knee Arthroplasty Using Patient-Specific Templating", Clinical Orthopaedics and Related Research, 444, 184-192, 2006 (9 pages).

"Insall/Burstein II Surgical Technique", Constrained Condylar Modular Knee System, Zimmer, (18 pages).

Berry, Seedhom, et al., "Personalised image-based templates for intra-operative guidance," Proceedings of the Institution of Mechanical Engineers, Part H: Journal of Engineering in Medicine, 111-118, 2005.

SurgiTAIX AG, "OrthoTAIX for Orthopaedic Surgery." Available at http://www.surgitaix.com/Products/OrthoTAIX/OrthoTAIX.pdf.

Radermacher et al., "Computer-Integrated Orthopaedic Surgery: Connection of Planning and Execution in Surgical Intervention," Computer Integrated Surgery, 451-463, 1995.

Radermacher et al., "CT Image-Based Planning and Execution of Interventions in Orthopedic Surgery Using Individual Templates—Experimental Results and Aspects of Clinical Applications," Computer Assisted Orthopaedic Surgery, L.P Nolte and R. Ganz, eds, 42-52, Hogrefe & Huber Publishing 1999.

PCT Search Report for International Application No. PCT/US2011/044466, filed Jul. 19, 2011, 4 pages.

PCT Search Report for Application PCT/US2008/078143 (17 pages).

International Preliminary Report on Patentability for International Patent Publication No. PCT/US2008/078143, Apr. 15, 2010, 8 pages.

European Search Report for European Patent Application No. 10150487.6-2310, May 12, 2010, 7 pages.

European Search Report for European Patent Application No. 09171188.7-2310, Sep. 24, 2010, 7 pages.

Customized Patient Instruments, Patient specific instruments for patient specific needs, brochure. (2008) DePuy Orthopaedics, Inc. 14 sheets.

Customized Patient Instruments, Primary Cruciate Retaining Surgical Technique for use with the Sigma® Knee System Utilizing Specialist® 2 Instrumentation, brochure. (2008) DePuy Orthopaedics, Inc. pp. 1-23.-

(56) References Cited

OTHER PUBLICATIONS

"TruMatch™ Personalized knee replacement solutions," tri-fold brochure. (2009) Sigma® DePuy Orthopaedics, Inc. 2 pages.

Murphy, S.B., et al. "The Hip Sextant: Navigation of Acetabular Component Orientation Using a Mechanical Instrument," brochure. (2009) 1 page.

Seel et al., "Three-Dimensional Planning and Virtual Radiographs in Revision Total Hip Arthroplasty for Instability", Clinical Orthopaedics and Related Research, No. 442, pp. 35-38, Jan. 2006.

Radermacher, "Development of a Clinical Demonstrater for Computer Assisted Orthopedic Surgery with CT-Image Based Individual Templates (chapter in Computer Assisted Radiology and Surgery, edited by H.U. Lemke, M.W. Vannier and K. Inamura)," (1997).

Radermacher, "Clinical Experience With the Individual Template Technique," (2001).

Radermacher, "Computer Assisted Orthopedic Surgery By Means of Individual Templates Aspects and Analysis of Potential Applications," (1994).

Radermacher, German Version "Potentials of CT-based Planning and Template-based Procedure in Hip and Knee Surgery," (2000).

Radermacher, English Translation of German Version "Potentials of CT-based Planning and Template-based Procedure in Hip and Knee Surgery," (2000).

Patent Cooperation Treaty, International Preliminary Report on Patentability, International Application No. PCT/US2011/044466, Dated February 12, 2013, 10 Pages.

* cited by examiner

CUSTOMIZED PATIENT-SPECIFIC ACETABULAR ORTHOPAEDIC SURGICAL INSTRUMENT AND METHOD OF USE AND FABRICATION

CROSS-REFERENCE TO RELATED APPLICATIONS

Cross-reference is made to U.S. patent application Ser. No. 12/543,156, which was filed on Aug. 18, 2009 and is expressly incorporated herein by reference.

TECHNICAL FIELD

The present disclosure relates generally to customized patient-specific orthopaedic surgical instruments and more particularly to customized patient-specific acetabular orthopaedic surgical instruments.

BACKGROUND

Joint arthroplasty is a well-known surgical procedure by which a diseased and/or damaged natural joint is replaced by a prosthetic joint. For example, in a hip arthroplasty surgical procedure, a prosthetic hip replaces a patient's natural hip. A typical prosthetic hip includes an acetabular orthopaedic prosthesis and/or femoral head orthopaedic prosthesis. A typical acetabular orthopaedic prosthesis includes an acetabular cup, which is secured to the patient's natural acetabulum, and an associated polymer/ceramic/metal bearing or ring.

To facilitate the replacement of the natural joint with an acetabular orthopaedic prosthesis, orthopaedic surgeons may use a variety of orthopaedic surgical instruments such as, for example, reamers, drill guides, drills, and/or other surgical instruments. Typically, such orthopaedic surgical instruments are generic with respect to the patient such that the same orthopaedic surgical instrument may be used on a number of different patients during similar orthopaedic surgical procedures.

SUMMARY

According to one aspect of the disclosure, a customized patient-specific orthopaedic instrument for facilitating implantation of an acetabular cup prosthesis in a coxal bone of a patient is disclosed. The customized patient-specific orthopaedic instrument includes a customized patient-specific acetabular reaming guide including a ring-shaped body having an inner surface defining a cylindrical passageway, and a plurality of arms extending from the ring-shaped body. Each of the ring-shaped body and the plurality of arms includes a bone-facing surface having a customized patient-specific negative contour that receives a corresponding positive contour of the patient's coxal bone. The cylindrical passageway defines a longitudinal axis that is oriented relative to the bone-facing surface of the ring-shaped body based on a predetermined version angle and a predetermined inclination angle of the acetabular cup prosthesis when the prosthesis is implanted in the patient's coxal bone.

In some embodiments, the customized patient-specific acetabular reaming guide may further include a guide housing configured to be secured to the ring-shaped body, and the guide housing may have a second inner surface defining a longitudinal passageway sized to receive an acetabular reamer surgical tool. Additionally, in some embodiments, the guide housing may include a depth stop to limit movement of the acetabular reamer surgical tool along the longitudinal axis. In some embodiments, the ring-shaped body may have a slot defined therein, and the guide housing may have a flange extending from a lower end thereof. The flange may be sized to be received in the slot of the ring-shaped body to secure the guide housing to the ring-shaped body.

In some embodiments, an angle may be defined between each arm of the plurality of arms with respect to another adjacent arm of the plurality of arms when viewed in the top plan view and each of the angles may have a magnitude different from any other angle. Additionally, in some embodiments, the plurality of arms may include at least three arms extending from the ring-shaped body. In some embodiments, the customized patient-specific negative contour of the bone-facing surface of at least one of the plurality of arms may receive the corresponding positive contour of the ilium of the patient's coxal bone. In some embodiments, each arm of the plurality of arms may include a surface defining a hole extending therethrough sized to receive a bone pin.

In some embodiments, the customized patient-specific negative contour of the bone-facing surface of the ring-shaped body may receive the corresponding positive contour of the acetabular margin of the patient's coxal bone. In some embodiments, the cylindrical passageway of the ring-shaped body may be sized to receive an acetabular reamer surgical tool.

According to another aspect, a customized patient-specific orthopaedic instrument includes a customized patient-specific acetabular reaming guide including a guide body and a guide housing securable the guide body. The guide body includes a bone-facing surface having a customized patient-specific negative contour that receives a corresponding positive contour of the patient's coxal bone, and an inner surface defining a cylindrical passageway extending therethrough, the cylindrical passageway defining a longitudinal axis oriented relative to the bone-facing surface based on a predetermined version angle and a predetermined inclination angle of the acetabular cup prosthesis when implanted in the patient's coxal bone. The guide housing includes a depth stop to limit movement of an acetabular reamer surgical tool along the longitudinal axis.

In some embodiments, the guide body may include a plurality of arms, and each arm of the plurality of arms may include a bone-facing surface having a customized patient-specific negative contour to receive a corresponding positive contour of the patient's coxal bone. In some embodiments, the guide body may have a slot defined therein extending orthogonally to the longitudinal axis, and the guide housing may have a flange extending from an end securable to the guide body. The flange may be sized to be received in the slot of the guide body to secure the guide housing to the guide body.

In some embodiments, the customized patient-specific orthopaedic instrument may further include the acetabular reamer surgical tool, which may include at least one reamer head to be separately secured to a reamer shank of the acetabular reamer surgical tool. Additionally, in some embodiments, the reamer shank may include a shaft having a flange extending outwardly therefrom. The flange may be positioned to contact the depth stop when the reamer head has advanced to a predetermined positioned relative to the bone-facing surface of the guide body. In some embodiments, the flange may be a depressible button. In some embodiments, the customized patient-specific acetabular reaming guide may be formed from a transparent material.

According to another aspect, a method of using a customized patient-specific acetabular reaming guide to perform an orthopaedic bone reaming procedure on a patient's acetabulum to facilitate implantation of an acetabular cup prosthesis in a coxal bone of the patient is disclosed. The method includes positioning a guide body of the customized patient-specific acetabular reaming guide such that a customized patient-specific negative contour defined in a bone-facing surface of the guide body receives a corresponding positive contour of the patient's coxal bone. The guide body has a cylindrical passageway that defines a longitudinal axis oriented relative to the bone-facing surface based on a predetermined version angle and a predetermined inclination angle of the acetabular cup prosthesis when implanted in the patient's coxal bone. The method also includes securing a guide housing of the customized patient-specific acetabular reaming guide to the guide body, advancing an acetabular reamer surgical tool along the longitudinal axis into the patient's acetabulum, and reaming the patient's acetabulum using the cylindrical passageway of the guide body and the guide housing as guides for the acetabular reamer surgical tool.

In some embodiments, the method may further include coupling a reamer shank to a reamer head of the acetabular reamer surgical tool, and positioning the acetabular reamer surgical tool within the guide housing prior to securing the guide housing to the guide body. Additionally, in some embodiments, reaming the patient's acetabulum may include advancing the reamer head to a predetermined depth into the acetabulum, wherein a flange of the reamer shank contacts with an upper end of the guide housing at the predetermined depth. In some embodiments, positioning the guide body may include positioning the guide body such that the customized patient-specific negative contour of the bone-facing surface receives a corresponding positive contour of the acetabular margin of the patient's coxal bone.

In some embodiments, the guide body may include at least one arm including a bone-facing surface having a customized patient-specific negative contour, and positioning the guide body may include positioning the at least one arm on the patient's coxal bone such that the customized patient-specific negative contour of the at least one arm receives a corresponding positive contour of the patient's coxal bone. In some embodiments, positioning the guide body may include positioning the at least one arm such that the customized patient-specific negative contour of the bone-facing surface receives the corresponding positive contour of the ilium of the patient's coxal bone. In some embodiments, the method may further include drilling a plurality of pilot holes into the patient's coxal bone using holes defined in the guide body as drill guides, and inserting a bone pin through each of the plurality of pilot holes and into each of the corresponding pilot holes formed in the patient's coxal bone.

BRIEF DESCRIPTION OF THE DRAWINGS

The detailed description particularly refers to the following figures, in which.

DETAILED DESCRIPTION OF THE DRAWINGS

Figure 1:
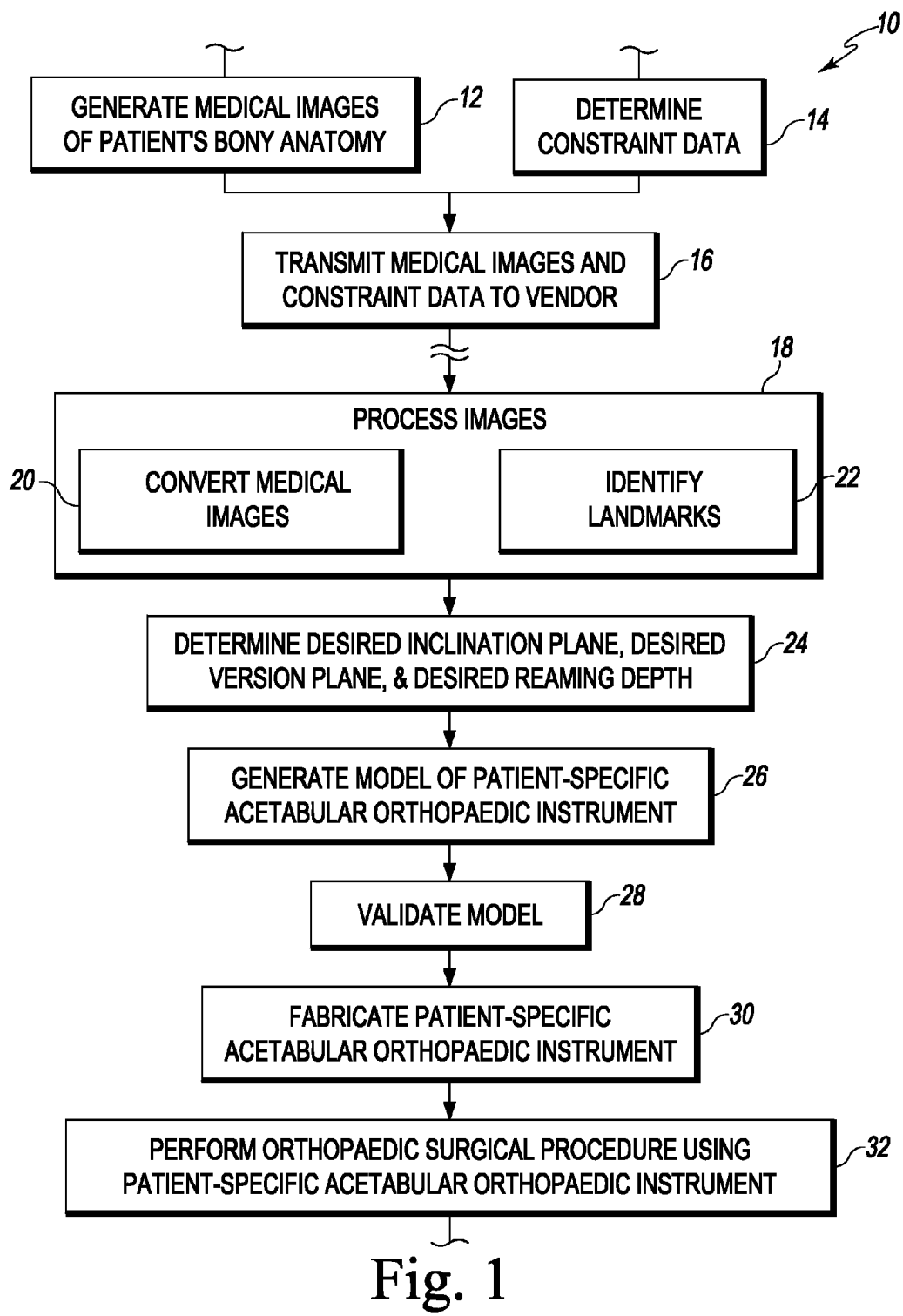
FIG. 1 is a simplified flow diagram of a method for designing and fabricating a customized patient-specific orthopaedic surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Referring to FIG. 1, an algorithm 10 for fabricating a customized patient-specific orthopaedic surgical instrument is illustrated. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient specific orthopaedic surgical instruments that are intended for use on a variety of different patients. Additionally, it should be appreciated that, as used herein, the term "customized patient-specific orthopaedic surgical instrument" is distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

In some embodiments, the customized patient-specific orthopaedic surgical instrument may be customized to the particular patient based on the location at which the instrument is to be coupled to one or more bones of the patient, such as in an area of the patient's coxal bone proximate to the acetabulum. For example, in some embodiments, the customized patient-specific orthopaedic surgical instrument may include one or more bone-contacting or facing surfaces having a negative contour that matches the contour of a portion of the relevant bone of the patient, which is discussed in more detail below in regard to FIG. 2. As such, the customized patient-specific orthopaedic surgical instrument is configured to be coupled to the patient's coxal bone in a unique location and position with respect to the patient's bony anatomy. That is, the negative contours of the bone-contacting surfaces are configured to receive a matching contour surface of the portion of the patient's coxal bone. As such, the orthopaedic surgeon's guesswork and/or intra-operative decision-making with respect to the placement of the patient-specific acetabular orthopaedic surgical instrument are reduced. For example, the orthopaedic surgeon may not be required to locate landmarks of the patient's bone to facilitate the placement of the patient-specific orthopaedic surgical instrument, which typically requires some amount of estimation on part of the surgeon. Rather, the orthopaedic surgeon may simply couple the customized patient-specific orthopaedic surgical instrument to the patient's coxal bone in the unique location. When so coupled, the patient-specific orthopaedic surgical instrument defines a particular degree of version and inclination angles relative to the acetabulum and the intended acetabular orthopaedic prosthesis.

As shown in FIG. 1, the method 10 includes steps 12 and 14, in which an orthopaedic surgeon performs pre-operative planning of the acetabular orthopaedic surgical procedure to be performed on a patient. The steps 12 and 14 may be performed in any order or contemporaneously with each other. In step 12, a number of medical images of the patient's acetabulum and the surrounding bony anatomy are generated. To do so, the orthopaedic surgeon or other healthcare provider may operate an imaging system to generate the medical images. The medical images may be embodied as any number and type of medical images capable of being used to generate a three-dimensional rendered model of the patient's acetabulum and surrounding bony anatomy. For example, the medical images may be embodied as any number of computed tomography (CT) images, magnetic resonance imaging (MRI) images, or other three-dimensional medical images. Additionally, or alternatively, as discussed in more detail below in regard to step 18, the medical images may be embodied as a number of X-ray images or other two-dimensional images from which a three-dimensional rendered model of the area of the patient's coxal bone proximate to the acetabulum and the surrounding bony anatomy may be generated.

In step 14, the orthopaedic surgeon may determine any additional pre-operative constraint data. The constraint data may be based on the orthopaedic surgeon's preferences, preferences of the patient, anatomical aspects of the patient, guidelines established by the healthcare facility, or the like. For example, the constraint data may include the orthopaedic surgeon's preference for the amount of inclination and version for the acetabular prosthesis, the implant depth of the acetabular prosthesis, the amount of the bone to ream, the size range of the orthopaedic implant, and/or the like. In some embodiments, the orthopaedic surgeon's preferences are saved as a surgeon's profile, which may be used as a default constraint values for further surgical plans.

In step 16, the medical images and the constraint data, if any, are transmitted or otherwise provided to an orthopaedic surgical instrument vendor or manufacturer. The medical images and the constraint data may be transmitted to the vendor via electronic means such as a network or the like. After the vendor has received the medical images and the constraint data, the vendor processes the images in step 18. The orthopaedic surgical instrument vendor or manufacturer processes the medical images to facilitate the determination of the proper planes of inclination and version, implant depth, implant sizing, and fabrication of the customized patient-specific orthopaedic surgical instrument, as discussed in more detail below.

In step 20, the vendor may convert or otherwise generate three-dimensional images from the medical images. For example, in embodiments wherein the medical images are embodied as a number of two-dimensional images, the vendor may use a suitable computer algorithm to generate one or more three-dimensional images form the number of two-dimensional images. Additionally, in some embodiments, the medical images may be generated based on an established standard such as the Digital Imaging and Communications in Medicine (DICOM) standard. In such embodiments, an edge-detection, thresholding, watershed, or shape-matching algorithm may be used to convert or reconstruct images to a format acceptable in a computer aided design application or other image processing application.

In step 22, the vendor may process the medical images, and/or the converted/reconstructed images from step 20, to determine a number of aspects related to the bony anatomy of the patient such as the anatomical axis of the patient's bones, the mechanical axis of the patient's bone, other axes and various landmarks, and/or other aspects of the patient's bony anatomy. To do so, the vendor may use any suitable algorithm to process the images.

In step 24, the desired inclination plane, the desire version plane, and the desired reaming depth for implantation of the acetabular orthopaedic prosthesis are determined. Each of those variables may be determined based on the type, size, and/or position of the acetabular orthopaedic prosthesis to be used during the orthopaedic surgical procedure; the process images, such as specific landmarks identified in the images; and the constraint data supplied by the orthopaedic surgeon in steps 14 and 16. The type and/or size of the acetabular orthopaedic prosthesis may be determined based on the patient's anatomy and the constraint data. For example, the constraint data may dictate the type, make, model, size, or other characteristic of the acetabular orthopaedic prosthesis. The selection of the acetabular orthopaedic prosthesis may also be modified based on the medical images such that an acetabular orthopaedic prosthesis that is usable with the acetabulum of the patient and that matches the constraint data or preferences of the orthopaedic surgeon is selected.

In addition to the type and size of the acetabular orthopaedic prosthesis, the planned location and position of the acetabular orthopaedic prosthesis relative to the patient's bony anatomy is determined. To do so, a digital template of the acetabular orthopaedic prosthesis may be overlaid onto one or more of the processed medical images. The vendor may use any suitable algorithm to determine a recommended location and orientation of the acetabular orthopaedic prosthesis (i.e., the digital template) with respect to the patient's bone based on the processed medical images (e.g., landmarks of the patient's acetabulum defined in the images) and/or the constraint data. Additionally, any one or more other aspects of the patient's bony anatomy may be used to determine the proper positioning of the digital template.

In some embodiments, the digital template along with surgical alignment parameters may be presented to the orthopaedic surgeon for approval. The approval document may include the implant's planned inclination and version planes, the planned depth to which the surgeon plans to ream, the orientation of the transverse acetabular ligament and labrum, and other relevant landmarks of the patient's bony anatomy.

The proper inclination and version planes for the acetabular orthopaedic prosthesis may then be determined based on the determined size, location, and orientation of the acetabular orthopaedic prosthesis. In addition, other aspects of the patient's bony anatomy, as determined in step 22, may be used to determine or adjust the planned inclination and version planes. For example, the determined mechanical axis, landmarks, and/or other determined aspects of the relevant bones of the patient may be used to determine the planned inclination and version planes.

In step 26, a model of the customized patient-specific orthopaedic surgical instrument, which in the illustrative embodiment is a customized patient-specific acetabular orthopaedic surgical instrument, is generated. In some embodiments, the model is embodied as a three-dimensional rendering of the customized patient-specific acetabular orthopaedic surgical instrument. In other embodiments, the model may be embodied as a mock-up or fast prototype of the customized patient-specific acetabular orthopaedic surgical instrument. The patient-specific acetabular orthopaedic surgical instrument to be modeled and fabricated may be determined based on the acetabular orthopaedic surgical procedure to be performed, the constraint data, and/or the type of orthopaedic prosthesis to be implanted in the patient.

The particular shape of the customized patient-specific acetabular orthopaedic surgical instrument is determined based on the planned location and implantation angles of the acetabular orthopaedic prosthesis relative to the patient's acetabulum. The planned location of the customized patient-specific acetabular orthopaedic surgical instrument relative to the patient's acetabulum may be selected based on, in part, the planned inclination and version planes of the patient's acetabulum as determined in step 24. For example, in some embodiments, the customized patient-specific acetabular orthopaedic surgical instrument is embodied as an acetabular reaming guide. In such embodiments, the location of the acetabular reaming guide is selected such that the acetabular reaming guide is usable to position the acetabular orthopaedic prosthesis at the planned inclination and version planes determined in step 24. Additionally, the planned location of the orthopaedic surgical instrument may be based on the identified landmarks of the patient's acetabulum identified in step 22.

In some embodiments, the particular shape or configuration of the customized patient-specific acetabular orthopaedic surgical instrument may be determined based on the planned location of the instrument relative to the patient's bony anatomy. That is, the customized patient-specific acetabular orthopaedic surgical instrument may include a bone-contacting surface having a negative contour that matches the corresponding contour of a portion of the bony anatomy of the patient such that the orthopaedic surgical instrument may be coupled to the bony anatomy of the patient in a unique location, which corresponds to the pre-planned location for the instrument. When the orthopaedic surgical instrument is coupled to the patient's bony anatomy in the unique location, one or more guides (e.g., cutting or drilling guide) of the orthopaedic surgical instrument may be aligned to the inclination and version planes, as discussed above.

After the model of the customized patient-specific acetabular orthopaedic surgical instrument has been generated in step 26, the model is validated in step 28. The model may be validated by, for example, analyzing the rendered model while coupled to the three-dimensional model of the patient's anatomy to verify the correlation of reaming guides, inclination and version planes, and/or the like. Additionally, the model may be validated by transmitting or otherwise providing the model generated in step 26 to the orthopaedic surgeon for review. For example, in embodiments wherein the model is a three-dimensional rendered model, the model along with the three-dimensional images of the patient's acetabulum and area of the coxal bone proximate to the acetabulum may be transmitted to the surgeon for review. In embodiments wherein the model is a physical prototype, the model may be shipped to the orthopaedic surgeon for validation.

After the model has been validated in step 28, the customized patient-specific acetabular orthopaedic surgical instrument is fabricated in step 30. The customized patient-specific acetabular orthopaedic surgical instrument may be fabricated using any suitable fabrication device and method. Additionally, the customized patient-specific acetabular orthopaedic instrument may be formed from any suitable material such as a metallic material, a plastic material, or combination thereof depending on, for example, the intended use of the instrument. The fabricated customized patient-specific acetabular orthopaedic instrument is subsequently shipped or otherwise provided to the orthopaedic surgeon. The surgeon performs the orthopaedic surgical procedure in step 32 using the customized patient-specific acetabular orthopaedic surgical instrument. As discussed above, because the orthopaedic surgeon does not need to determine the proper location of the orthopaedic surgical instrument intra-operatively, which typically requires some amount of estimation on part of the surgeon, the guesswork and/or intra-operative decision-making on part of the orthopaedic surgeon is reduced.

It should also be appreciated that variations in the bony anatomy of the patient may require more than one customized patient-specific acetabular orthopaedic surgical instrument to be fabricated according to the method described herein. For example, the patient may require the implantation of two acetabular orthopaedic prostheses to replace both natural hips. As such, the surgeon may follow the method 10 of FIG. 1 to fabricate a different customized patient-specific acetabular orthopaedic surgical instrument for use in replacing each natural hip. Each customized patient-specific acetabular orthopaedic surgical instrument defines a particular degree of version angle and a particular degree of inclination angle relative to each particular acetabulum that is different due to the variation in the bony anatomy of each hip.

Figure 2:
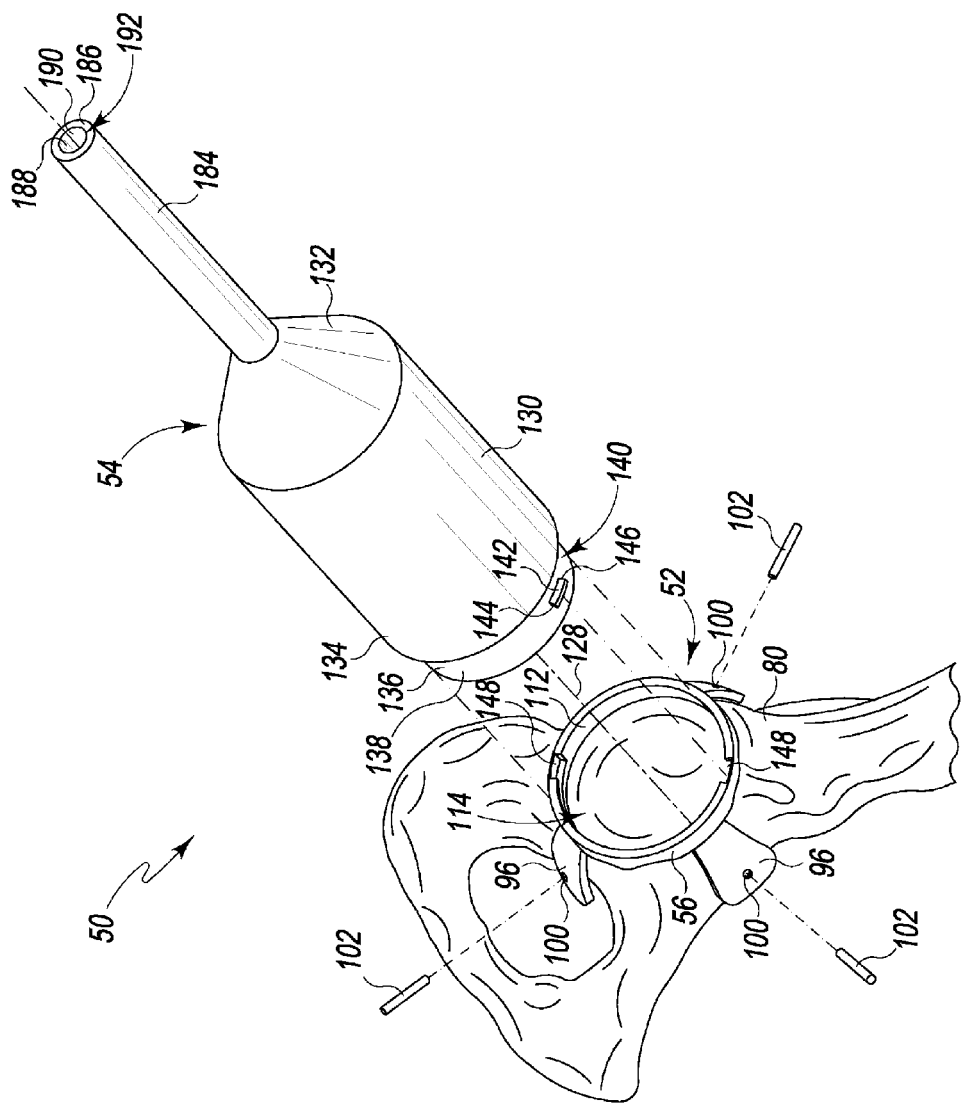
FIG. 2 is an exploded perspective view of one embodiment of a customized patient-specific orthopaedic surgical instrument.
Figure 3:
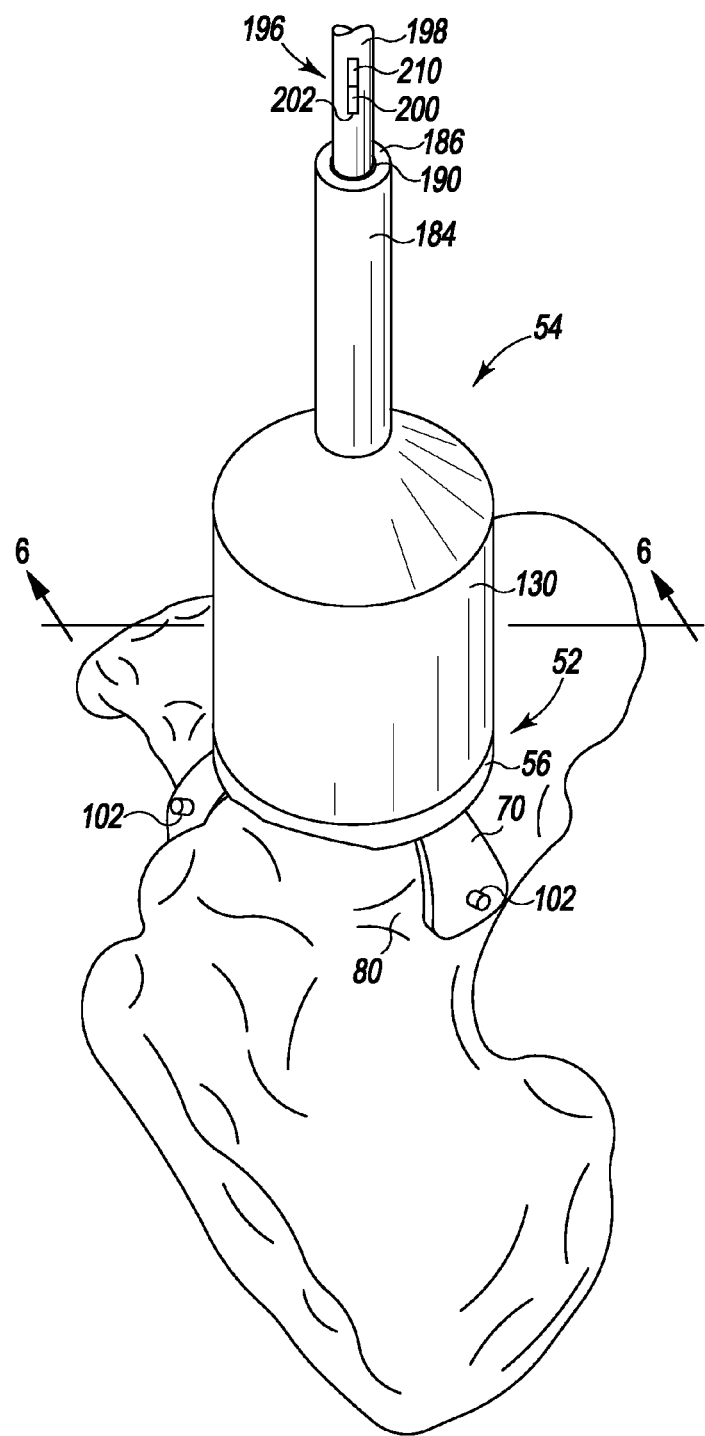
FIG. 3 is a perspective view of the customized patient-specific orthopaedic surgical instrument of FIG. 2 in an assembled configuration.

Referring now to FIGS. 2 and 3, the customized patient-specific acetabular orthopaedic surgical instrument is illustratively embodied as a customized patient-specific acetabular reaming guide 50 (hereinafter reaming guide 50). The reaming guide 50 includes a locating base 52 and a sheath or housing 54 configured to be secured to the base 52, as will be described in greater detail below. The base 52 and the housing 54 may be formed from any suitable material such as, for example, a resilient plastic or metallic material. In one particular embodiment, the reaming guide 50 is formed from injection-molded, clear polypropylene or other transparent material such that the interior of the reaming guide 50 is visible when the guide 50 is secured to the patient's bony anatomy. In other embodiments, the reaming guide 50 may be formed from implant-grade metallic material such as titanium or cobalt chromium. Additionally, the reaming guide 50 may include image intensifiers such as, for example, stainless steel, tantalum, or other dense material to aid in positioning and to check the accuracy of alignment.

Figure 4:
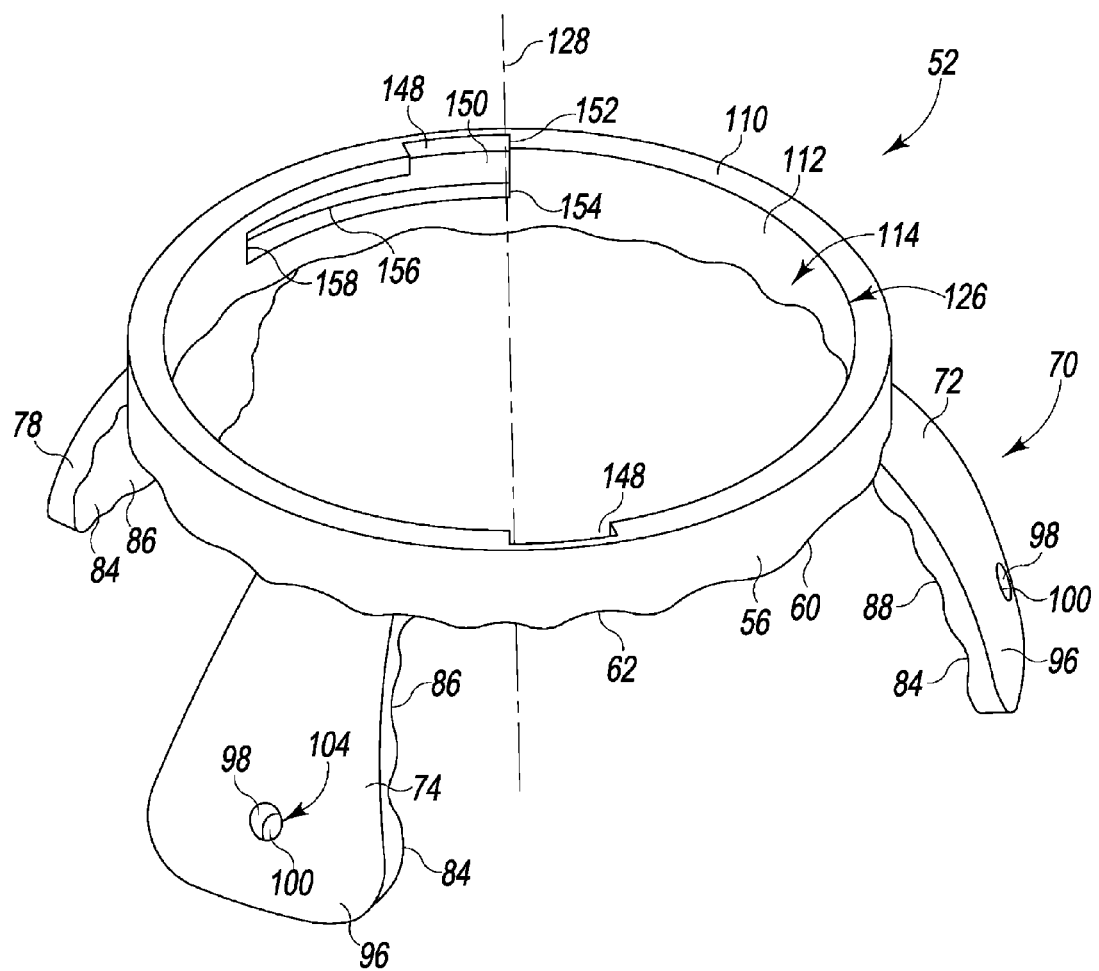
FIG. 4 is a perspective view of the guide body of the customized patient-specific orthopaedic surgical instrument of FIG. 2.

The base 52 includes a guide body 56 configured to contact a portion of the patient's coxal bone during use. In the illustrative embodiment, the guide body 56 has a generally ring shape but in other embodiments the guide body 56 could have a generally square shape, rectangular shape, or any other suitable form. As best seen in FIG. 4, the body 56 includes a bottom surface 60, which is configured to contact a portion of the area of the patient's coxal bone proximate to the acetabulum. In the illustrative embodiment, the bottom surface 60 includes a customized patient-specific negative contour 62 configured to receive the corresponding positive contour of the acetabular margin 64 of the patient's coxal bone (see FIG. 6). It should be appreciated that in other embodiments the bottom surface 60 may include other customized patient-specific negative contours that are configured to receive other corresponding contours of the patient's coxal bone proximate to the acetabulum.

The base 52 also includes a plurality of arms 70 extending outwardly from the body 56. In the illustrative embodiment of FIGS. 2-6, the body 56 and the arms 70 are formed as a single monolithic component. However, it should be appreciated that in other embodiments the body 56 and the arms 70 could each be formed from separate pieces. For example, the arms 70 may be separately secured to the body 56 via suitable fasteners such as screws, bolts, adhesive, or the like.

Figure 5:
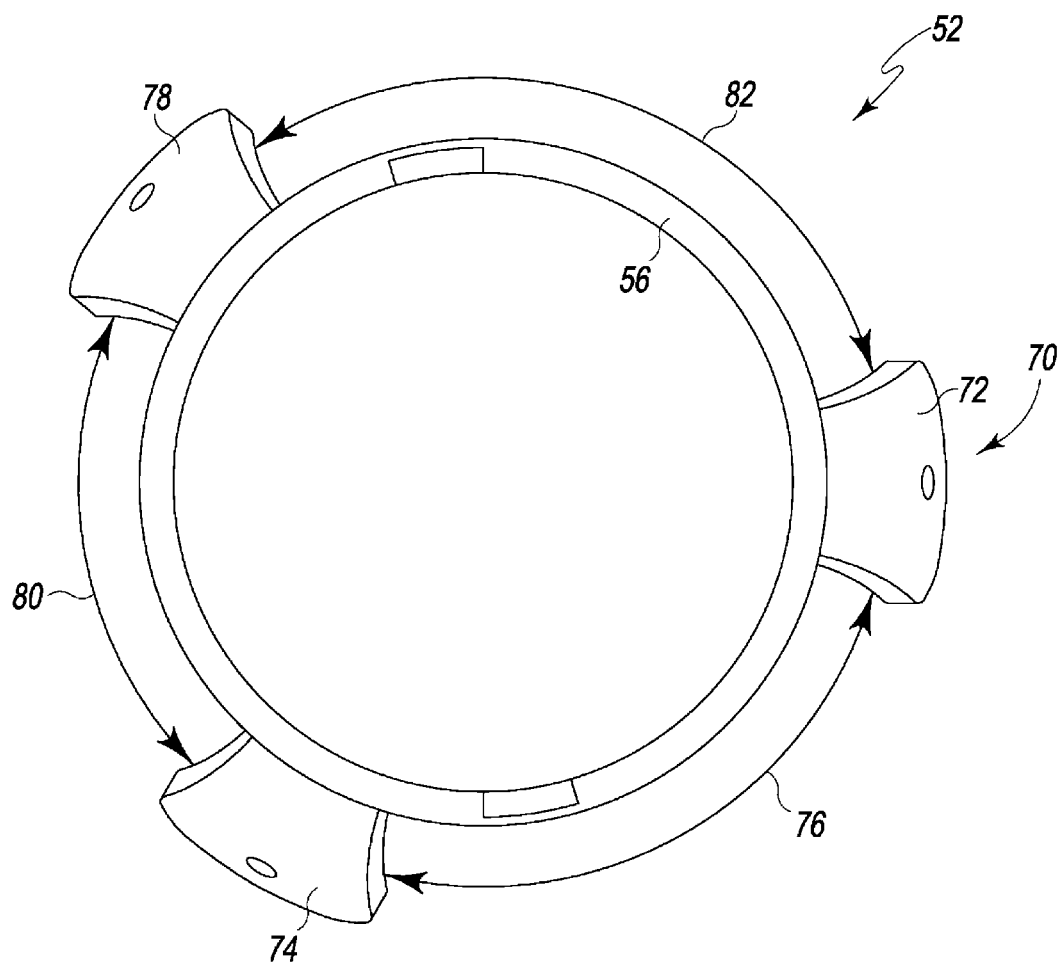
FIG. 5 is a top plan view of the guide body of the customized patient-specific orthopaedic surgical instrument of FIG. 2.

In the illustrative embodiment, the base 52 includes three arms 70 extending from the body 56. It should be appreciated that in other embodiments the base 52 may include additional or fewer arms depending on the patient's bony anatomy and the preference of the surgeon. When viewed from the top plan view of FIG. 5, the arms 70 extend from the body 56 in a configuration that defines an angle between each arm 70. For example, as illustrated in FIG. 5, an arm 72 and an arm 74 define an angle 76 therebetween, the arm 74 and an arm 78 define an angle 80 therebetween, and the arm 72 and the arm 78 define an angle 82 therebetween. The magnitude of each of the angles 76, 80, 82 is equal to approximately 120 degrees. In one particular embodiment, the arms 70 may extend from the body 56 such that the each of the angles 76, 80, 82 has a magnitude different from any other angle. Like many other dimensional characteristics described herein, the magnitude of the angles 76, 80, 82 may be customized to as required for the particular patient.

Each arm 70 is configured to contact a portion of the patient's coxal bone during use. Each arm 70 includes a bottom surface 84 that is configured to contact a portion of the area of the patient's coxal bone proximate to the acetabulum. Each bottom surface 84 includes a customized patient-specific negative contour 86 configured to receive a portion of the corresponding contour of the patient's coxal bone proximate to the acetabulum. In the illustrative embodiment, one arm 72 has a customized patient-specific negative contour 88 configured to receive the corresponding positive contour of the ilium 90 of the patient's coxal bone (see FIG. 2). It should be appreciated that in other embodiments bottom surfaces 84 may include other customized patient-specific negative contours that are configured to receive other corresponding contours of the patient's coxal bone proximate to the acetabulum. For example, the bottom surface 84 of another arm 70 may include a customized patient-specific negative contour configured to receive a corresponding contour of the pubis or the ischium of the patient's coxal bone. The contours 62, 86 of the base 52 cooperate to ensure the reaming guide 50 is placed on the patient's coxal bone in a desired position and orientation, which is based on the predetermined inclination plane and the predetermined version plane of the acetabular orthopaedic prosthesis.

Each arm 70 includes a top surface 96 positioned opposite the bottom surface 84. Each arm 70 also includes an inner surface 98 that defines a passageway 100 extending through each arm 70. The passageways 100 are sized to receive a corresponding bone pin 102 to be secured to the patient's coxal bone (see FIG. 2). The bone pins 102 cooperate to lock the base 52 in the unique position and orientation. It should be appreciated that in other embodiments the passageway 100 may be sized to receive wire or other retaining devices suitable for locking the base 52 into place on the coxal bone.

As shown in FIG. 4, each passageway 100 is angled relative to the top surface 96 and the bottom surface 84. Each passageway 100 has a diameter 104 that is slightly larger than the outer diameter of the pin 102, and the passageway 100 of each arm 70 has a substantially circular cross-section. It should be appreciated that in other embodiments each arm 70 may include a passageway 100 configured to receive a bone pin with a different cross-sectional shape. It will also be appreciated that the passageway 100 may have any cross-sectional shape suitable for receiving a drill bit of a bone drill and passing a bone pin therethrough.

Figure 6:
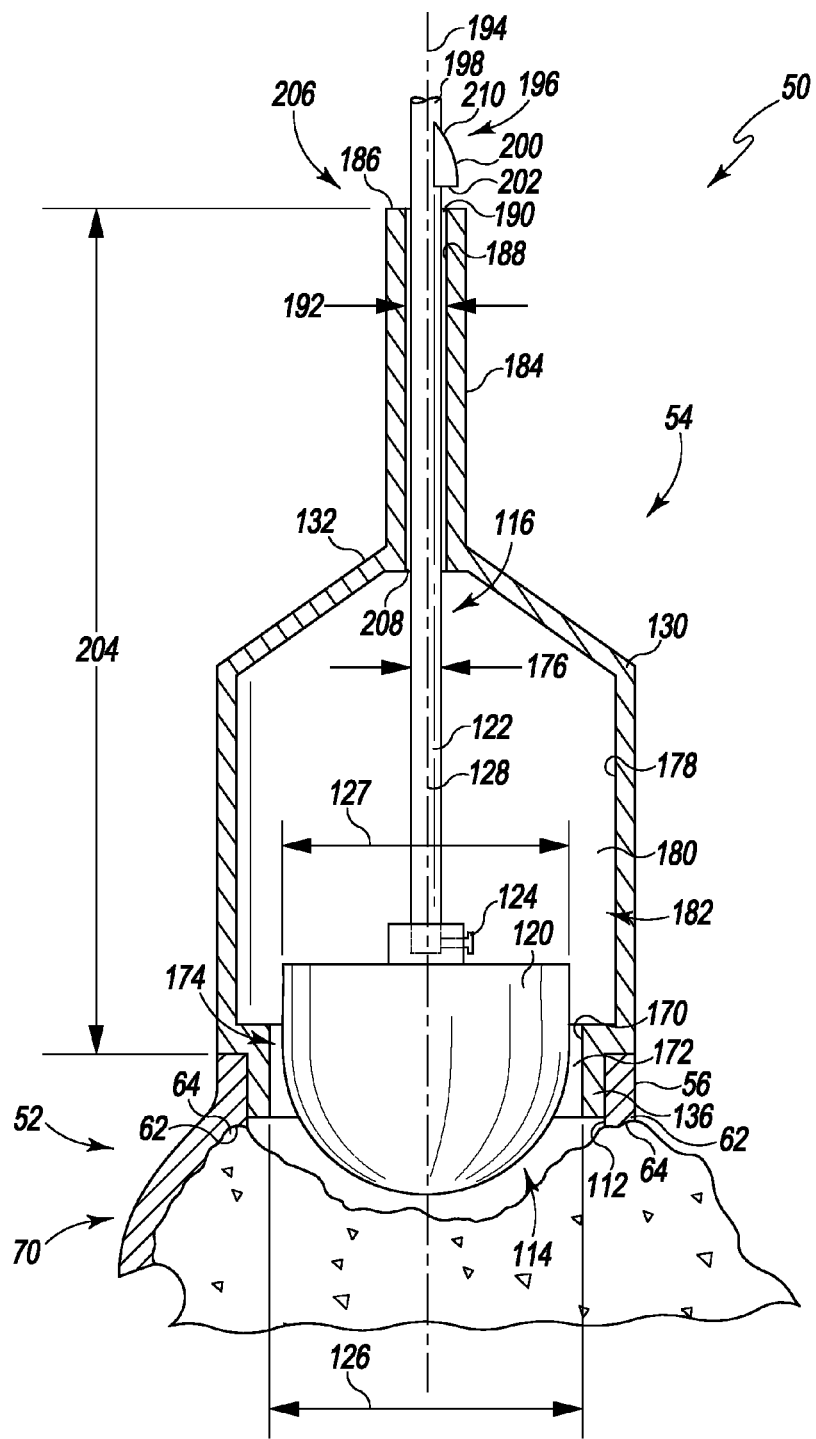
FIG. 6 is a cross-sectional view of the customized patient-specific orthopaedic surgical instrument of FIG. 3 taken along the line 6-6.

The guide body 56 includes a top surface 110 positioned opposite the bottom surface 60. An inner surface 112 connects the top surface 110 to the bottom surface 60 and defines an illustratively cylindrical passageway 114 extending therebetween. As shown in FIG. 6, the passageway 114 is sized such that an acetabular reamer surgical tool 116 may be moved through the passageway 114 and placed into contact with the patient's acetabulum. The acetabular reamer surgical tool 116 includes a reamer head 120 removably secured to a reamer shank 122 via a set screw 124. One example of an illustrative acetabular reamer surgical tool useable with the reaming guide 50 is the DePuy Quickset® Acetabular Grater System, which is commercially available from DePuy Orthopaedics, Inc. of Warsaw, Ind. U.S.A.

In the illustrative embodiment, the cylindrical passageway 114 of the base 52 includes a diameter 126 that is larger than the outer diameter 127 of the reamer head 120 to allow the reamer head 120 to advance therethrough. The passageway 114 of the body 56 defines a longitudinal axis 128 that is oriented relative to the bottom surface 60 of the body 56 based on the predetermined version angle and the predetermined inclination angle of the acetabular cup prosthesis. As shown in FIGS. 2-6, the axis 128 extends generally perpendicular to the bottom surface 60. In other embodiments, the axis 128 may be angled in one or more directions relative to the bottom surface 60 depending on the predetermined inclination and version angles for the particular patient. As will be discussed in greater detail below, the acetabular reamer surgical tool 116 is limited to movement along the axis 128 while being used to shape the patient's acetabulum. In that way, the reaming guide 50 ensures that the patient's acetabulum is shaped to receive the acetabular prosthesis according to the predetermined inclination and version angles.

Returning to FIG. 2, the reaming guide 50 also includes the housing 54 that is securable to the locating base 52. The housing 54 has a cylindrical main body 130 extending from an upper end 132 to a lower end 134. A sleeve 136 extends outwardly from the lower end 134 and includes an outer surface 138. The outer surface 138 has a diameter 140 that is less than the diameter 118 of the passageway 114 of the guide body 56. When the housing 54 is secured to the base 52, the sleeve 136 is positioned in the passageway 114 (see FIG. 6).

The sleeve 136 also illustratively includes a pair of flanges 142 projecting outwardly from the outer surface 138 of the sleeve 136. The flanges 142 are spaced apart from the lower end 134 of the main body 130 and extend in an arc about the circumference of the sleeve 136. In the illustrative embodiment, the flanges 142 have substantially the same length but in other embodiments the flanges 142 may have different lengths such that the housing 54 is keyed to the base 52.

The guide body 56 includes a pair of corresponding slots 148 defined therein that are configured to receive the flanges 142. Each slot 148 includes a notch 150 extending from an upper end 152 defined in the top surface 110 of the body 56 to a lower end 154 defined in the inner surface 112 of the body 56. Each slot 148 also includes a channel 156 defined in the inner surface 112 that extends from the lower end 154 of the notch 150 to a distal end 158. The length of the channel 156 substantially corresponds to the length of the flange 142. As best seen in FIG. 4, the channel 156 extends orthogonally to the longitudinal axis 128. It should be appreciated that in other embodiments the channel 156 may be tilted relative to the longitudinal axis 128 depending the desired position and orientation of the reaming guide 50 to further secure the housing 54 to the base 52.

The slots 148 and the flanges 142 cooperate to secure the housing 54 to the base 52. After the housing 54 is properly aligned with the base 52, the housing 54 may be placed in contact with the base 52 such that each flange 142 is received in the notch 150 of a corresponding slot 148. When the housing 54 is seated on the base 52, a bottom 160 of each flange 142 located in the lower end 154 of the notch 150. The housing 54 is then rotated about the longitudinal axis 128 to advance each flange 142 into the channel 156 of the corresponding slot 148 until an end 146 of the flange 142 is placed in contact with the end 158 of the channel 156 to secure the housing 54 to the base 52.

It should be appreciated that in other embodiments the reaming guide 50 may include additional or fewer flanges 142 and slots 148. Additionally, it should be appreciated that in other embodiments the housing 54 may be securable to the base 52 by other methods. For example, the sleeve 136 may have an external thread and the body 56 may have a corresponding internal thread. In such embodiments, the sleeve 136 may be threaded onto the body 56. In other embodiments, the housing 54 may include a latching mechanism secured to the main body 130 that engages with the base 52. Similarly, the housing 54 may be secured to the base 52 via suitable fasteners such as screws, bolts, or the like.

As best seen in FIG. 6, the sleeve 136 includes an inner surface 170 that defines a lower passageway 172. The lower passageway 172 has a diameter 174 that is slightly larger than the outer diameter 176 of the reamer head 120 of the acetabular reamer surgical tool 116. As such, the lower passageway 172 is sized such that the acetabular reamer surgical tool 116 may be moved along the longitudinal axis 128 and placed into contact with the patient's acetabulum. The main body 130 also includes an inner surface 178 that defines a central passageway 180 connected with the lower passageway 172. The central passageway 180 has a diameter 182 that is larger than the diameter 174 of the passageway 172. However, in other embodiments, the diameter 182 of the central passageway 180 may be substantially equal to the diameter 174 of the lower passageway 172.

A hollow shaft 184 extends upwardly from the upper end 132 of the main body 130. The shaft 184 includes an inner surface 188 that defines a cylindrical passageway 190 extending from a top end 186 of the shaft 184 to the upper end 132 of the main body 130. As shown in FIG. 6, the passageway 190 is fluidly connected with the central passageway 180 of the main body 130. The passageway 190 has an inner diameter 192 that is smaller than the diameters 174, 182 of the passageways 172, 180 and that is only slightly larger than the outer diameter 176 of the reamer shank 122 of the acetabular reamer surgical tool 116.

The passageway 190 of the shaft 184 defines another longitudinal axis 194 that is aligned or collinear with the axis 128 defined by the passageway 114 of the body 56. When the acetabular reamer surgical tool 116 is positioned as shown in FIG. 6, the close pairing of the diameters 176, 192 inhibits relative motion of the acetabular reamer surgical tool 116, thereby substantially limiting the acetabular reamer surgical tool 116 to movement along the axes 128, 194.

In the illustrative embodiment, the reamer shank 122 includes a user-depressible button 196 positioned proximate to a shank end 198, which is located external to the housing 54. The button 196 is moveable between an extended position, which is shown in FIG. 6, and a depressed position. When the button 196 is in the extended position, the button 196 extends outwardly from the shank 122 and includes an outer surface 200. When pressure is applied to the outer surface 200 of the button 196, the button 196 may be moved to the depressed position where the outer surface 200 is flush with the outer surface of the shank 122. A biasing member such as a spring (not shown) urges the button 196 to move from the depressed position to the extended position when pressure is removed from the outer surface 200.

The button 196 also has a lower surface 202, and, when the button 196 is the extended position, the reamer shank 122 is permitted to advance down the shaft 184 until the lower surface 202 contacts the top end 186 of the shaft 184. In that way, the longitudinal movement of the acetabular reamer surgical tool 116 along the axes 128, 194 relative to the bottom surface 60 of the body 56, and, by extension, the patient's acetabulum, is limited by the housing 54.

As shown in FIG. 6, the main body 130 and the shaft 184 define a total length 204. The magnitude of the length 204 is set based on the predetermined depth to which the orthopaedic surgeon plans to ream the patient's acetabulum. For example, when the surgeon desires to remove a greater amount of material from the patient's acetabulum, the length 204 may be of smaller magnitude so that the button 196 is placed in contact with the top end 186 of the shaft 184 after the reamer head 120 has advanced beyond the bottom surface 60 of the body 56 to a greater depth within the patient's acetabulum. In that way, the top end 186 of the shaft 184 acts a depth stop 206 for the acetabular reamer surgical tool 116, ensuring that the reamer head 120 is permitted to advance no further than a predetermined position relative to the bottom surface 60 of the body 56. In other words, reaming guide 50 permits the acetabular reamer surgical tool 116 to ream the patient's acetabulum to only a predetermined depth.

It should be appreciated that in other embodiments the shaft 184 may be a telescopic tube such that the surgeon may adjust the length 204 intra-operatively or pre-operatively according to surgical conditions. It will also be appreciated that in other embodiments the shank 122 may include a moveable collar rather than the button 196. In such embodiments, the surgeon could adjust the position of the collar along the shank 122 intra-operatively or pre-operatively in order to adjust the reaming depth.

Figure 7:
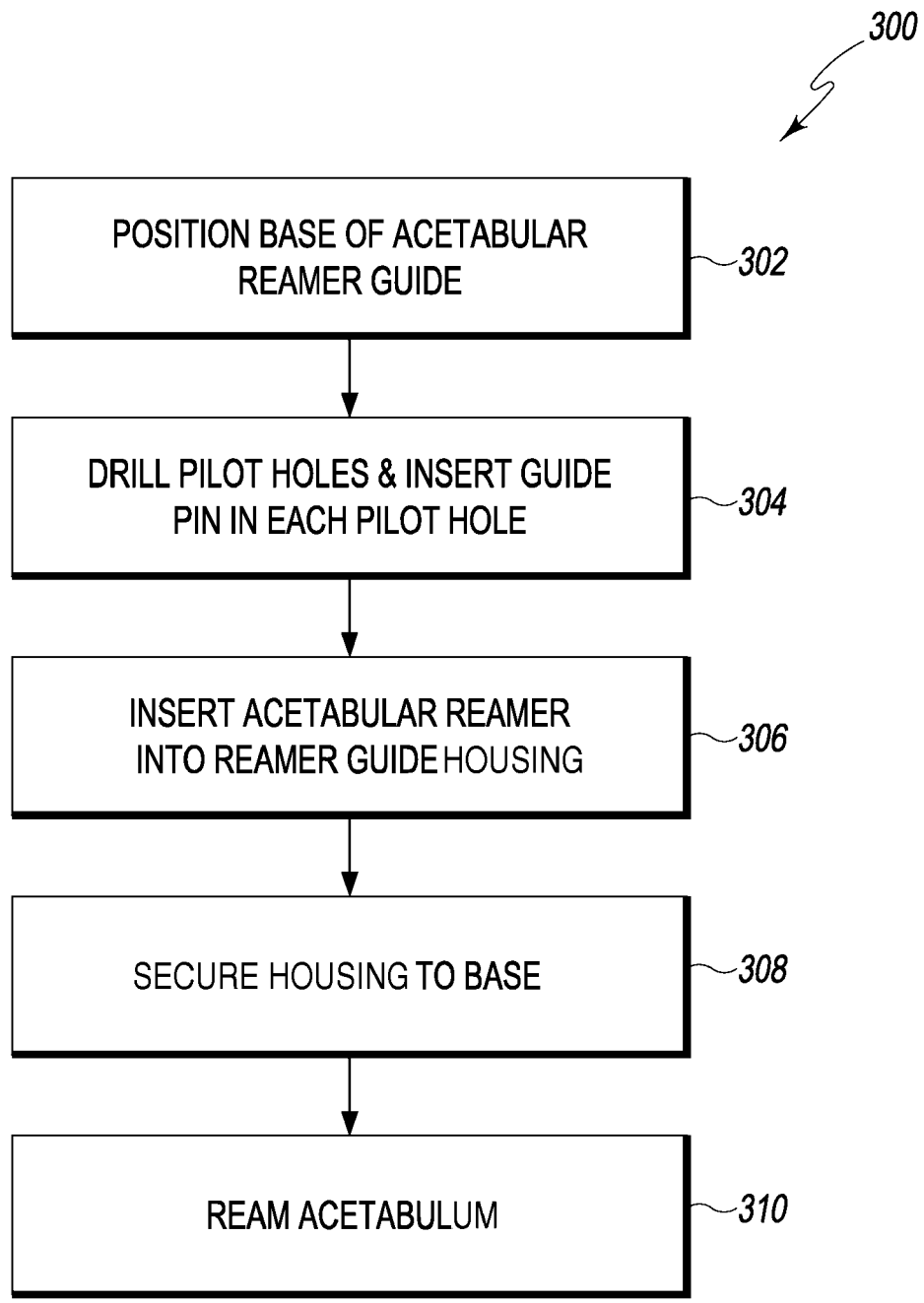
FIG. 7 is a simplified flow diagram of a method of performing an acetabular orthopaedic surgical procedure.

Referring to FIG. 7, an orthopaedic surgical procedure 300 using the reaming guide 50 is illustrated. The surgeon may perform the procedure 300 in step 32 of method 10, which is illustrated in FIG. 1 and described above. In step 302, the surgeon positions the locating base 52 of the reaming guide 50 on the patient's coxal bone. Because the locating base 52 is customized to the particular patient, the base 52 is positioned on the patient's coxal bone in a substantially unique, predetermined location and orientation.

Because the bottom surfaces 60, 84 of the base 52 include customized patient-specific contours 62, 86, the base 52 is positioned on the patient's coxal bone such that the corresponding contours of the surface of the patient's coxal bone are received in the negative contours 62, 86 of the base 52. For example, when the base 52 is properly positioned, the contour 62 of the body 56 receives the corresponding positive contour of the acetabular margin 64 of the patient's coxal bone. The customized patient-specific negative contour 88 of the arm 72 also receives the corresponding positive contour of the ilium 90 of the patient's coxal bone when the base 52 is properly positioned. The customized patient-specific negative contours 86 of the remaining arms 74, 78 similarly receive the corresponding positive contours of the surface of the patient's coxal bone. Once located in the unique position and orientation, the locating base 52 is aligned with the predetermined inclination and version angles relative to the patient's acetabulum intended for the acetabular orthopaedic prosthesis as determined in step 24 of the method 10. The longitudinal axis 128 further defines the path to be followed by the acetabular reamer surgical tool 116 during the reaming operation.

In step 304, the surgeon secures the base 52 to the coxal bone. The surgeon drills a pilot hole in the patient's coxal bone proximate to the acetabulum using each of the passageways 100 as drilling guides. The surgeon may then insert a bone pin 102 through each of the passageways 100 of the arms 70 and into the corresponding pilot hole defined in the patient's coxal bone.

In step 306, the surgeon inserts the acetabular reamer surgical tool 116 into the housing 54. In the illustratively embodiment, the surgeon selects the reamer head 120 and secures the head 120 to the reamer shank 122 using the set screw 124. The end 198 of the shank 122 may be inserted into the lower passageway 172 of the sleeve 136 of the housing 54, and the shank 122 may be advanced through the central passageway 180 to the upper end 132 of the main body 130. As the end 198 of the shank 122 passes into the passageway 190 of the shaft 184 through a lower end 208 thereof, a sloped or ramped end 210 of the button 196 may be advanced into contact with the inner surface 188 of the shaft 184 at the lower end 208. The contact between the inner surface 188 and the sloped end 210 as the shank 122 is advanced along passageway 190 causes the button 196 to move to the depressed position.

The button 196 remains in the depressed position as the shank 122 is advanced along the passageway 190. When the button 196 exits the top end 186 of the shaft 184, the biasing member urges the button 196 to move from the depressed position to the extended position. In that way, the button 196 ensures that the acetabular reamer surgical tool 116 is not inadvertently decoupled from the housing 54. Should the surgeon desire to remove the acetabular reamer surgical tool 116 from the housing 54, the surgeon may simply press the button 196 to move the button 196 to the depressed position before sliding the shank 122 back down the passageway 190.

In step 308, the housing 54 is secured to the locating base 52. To do so, the housing 54 is first aligned with the base 52 as shown in FIG. 2. The housing 54 is placed in contact with the base 52 such that each flange 142 is received in the notch 150 of a corresponding slot 148. The bottom 160 of each flange 142 is placed in contact with the lower end 154 of the notch 150. The housing 54 may then be rotated about the longitudinal axis 128 to advance each flange 142 into the channel 156 of the corresponding slot 148 until the end 146 of the flange 142 is placed in contact with the end 158 of the channel 156.

In step 310, the surgeon attaches a surgical drill to the end 198 of the shank 122 and begins to ream the patient's acetabulum. Because the locating base 52 was secured to the patient's acetabulum in a desired location and orientation based on the predetermined version and inclination angles of the acetabular prosthesis, the reaming of the patient's acetabulum is guided so as to size the patient's acetabulum to receive the acetabular prosthesis according to those predetermined angles. The surgeon advances the reamer head 120 into the patient's acetabulum until the button 196 is placed in contact with the depth stop 206. At that point, the reamer head 120 is located at a predetermined position relative to the bottom surface 60 of the body 56, and the surgeon has reamed the patient's acetabulum to the predetermined depth.

It should be appreciated that the surgeon may repeat any and all of the steps set forth above depending on the nature of the surgical procedure. For example, the surgeon may use more than one reamer head 120 to size the patient's acetabulum, beginning with a smaller head and progressively increasing the size of the head until the predetermined amount of material is removed. Similarly, the reaming guide 50 may include more than one housing 54, and each housing 54 may have a different length 204 to progressively adjust the reaming depth to permit the surgeon to remove greater amounts of material.

It should also be appreciated that the locating base 52 and the housing 54 may be used as a platform for other surgical instruments to assist with cup and liner placement. For example, the impacter used to seat the acetabular cup and liner may be provided with a shaft of the same diameter as the reamer shank 122. The locating base 52 and the housing 54 may then be used to guide the motion of the impacter to properly seat the acetabular cup and liner. Additionally, the locating base 52 may be used to provide visual confirmation of the placement of the acetabular cup and liner. The locating base 52 and/or the housing 54 may also include markings or graduations to provide information to the surgeon when performing inter-operative changes or when making adjustments to the size and/or alignment of the acetabular cup and liner.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It should be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A customized patient-specific orthopaedic instrument for facilitating implantation of an acetabular cup prosthesis in a coxal bone of a patient, the customized patient-specific orthopaedic instrument comprising:
a customized patient-specific acetabular reaming guide comprising (i) a ring-shaped body having an inner surface defining a cylindrical passageway, (ii) a plurality of arms extending from the ring-shaped body, and (iii) a guide housing configured to be secured to the ring-shaped body, the guide housing having a second inner surface defining a longitudinal passageway sized to receive an acetabular reamer surgical tool,
wherein (i) each of the ring-shaped body and the plurality of arms includes a bone-facing surface having a customized patient-specific negative contour configured to receive a corresponding positive contour of the patient's coxal bone, and (ii) the cylindrical passageway defines a longitudinal axis that is oriented relative to the bone-facing surface of the ring-shaped body based on a predetermined version angle and a predetermined inclination angle of the acetabular cup prosthesis when implanted in the patient's coxal bone.

2. The customized patient-specific orthopaedic instrument of claim 1, wherein the guide housing includes a depth stop to limit movement of the acetabular reamer surgical tool along the longitudinal axis.

3. The customized patient-specific orthopaedic instrument of claim 1, wherein the ring-shaped body has a slot defined therein, and the guide housing has a flange extending from a lower end thereof, the flange being sized to be received in the slot of the ring-shaped body to secure the guide housing to the ring-shaped body.

4. The customized patient-specific orthopaedic instrument of claim 1, wherein an angle is defined between each arm of the plurality of arms with respect to another adjacent arm of the plurality of arms when viewed in the top plan view and each of the angles has a magnitude different from any other angle.

5. The customized patient-specific orthopaedic instrument of claim 1, wherein the plurality of arms comprises at least three arms extending from the ring-shaped body.

6. The customized patient-specific orthopaedic instrument of claim 1, wherein the customized patient-specific negative contour of the bone-facing surface of at least one of the plurality of arms receives the corresponding positive contour of the ilium of the patient's coxal bone.

7. The customized patient-specific orthopaedic instrument of claim 1, wherein each arm of the plurality of arms includes a surface defining a hole extending therethrough sized to receive a bone pin.

8. The customized patient-specific orthopaedic instrument of claim 1, wherein the customized patient-specific negative contour of the bone-facing surface of the ring-shaped body receives the corresponding positive contour of the acetabular margin of the patient's coxal bone.

9. The customized patient-specific orthopaedic instrument of claim 1, wherein the cylindrical passageway of the ring-shaped body is sized to receive an acetabular reamer surgical tool.

10. A customized patient-specific orthopaedic instrument for facilitating implantation of an acetabular cup prosthesis in a coxal bone of a patient, the customized patient-specific orthopaedic instrument comprising:
an acetabular reamer surgical tool including at least one reamer head configured to be separately secured to a reamer shank of the acetabular reamer surgical tool, and
a customized patient-specific acetabular reaming guide comprising:
a guide body including (i) a bone-facing surface having a customized patient-specific negative contour configured to receive a corresponding positive contour of the patient's coxal bone, and (ii) an inner surface defining a cylindrical passageway extending therethrough, the cylindrical passageway defining a longitudinal axis oriented relative to the bone-facing surface based on a predetermined version angle and a predetermined inclination angle of the acetabular cup prosthesis when implanted in the patient's coxal bone, and
a guide housing securable to the guide body, the housing having a depth stop to limit movement of acetabular reamer surgical tool along the longitudinal axis,
wherein the reamer shank includes a shaft having a flange extending outwardly therefrom, and the flange being positioned to contact the depth stop when the reamer head has advanced to a predetermined positioned relative to the bone-facing surface of the guide body.

11. The customized patient-specific orthopaedic instrument of claim 10, wherein the guide body includes a plurality of arms, each arm of the plurality of arms including a bone-facing surface having a customized patient-specific negative contour to receive a corresponding positive contour of the patient's coxal bone.

12. The customized patient-specific orthopaedic instrument of claim 11, wherein each arm of the plurality of arms includes a surface defining hole extending therethrough sized to receive a bone pin.

13. The customized patient-specific orthopaedic instrument of claim 10, wherein the guide body has a slot defined therein extending orthogonally to the longitudinal axis, and the housing has a flange extending from an end securable to the guide body, the flange being sized to be received in the slot of the guide body to secure the guide housing to the guide body.

14. The customized patient-specific orthopaedic instrument of claim 10, wherein the flange is a depressible button.

15. The customized patient-specific orthopaedic instrument of claim 10, wherein the customized patient-specific acetabular reaming guide is formed from a transparent material.

16. A customized patient-specific orthopaedic instrument for facilitating implantation of an acetabular cup prosthesis in a coxal bone of a patient, the customized patient-specific orthopaedic instrument comprising:
a customized patient-specific acetabular reaming guide comprising:
a guide body including (i) a bone-facing surface having a customized patient-specific negative contour configured to receive a corresponding positive contour of the patient's coxal bone, and (ii) an inner surface defining a cylindrical passageway extending therethrough, the cylindrical passageway defining a longitudinal axis oriented relative to the bone-facing surface based on a predetermined version angle and a predetermined inclination angle of the acetabular cup prosthesis when implanted in the patient's coxal bone, and
a guide housing securable the guide body, the housing having a depth stop to limit movement of an acetabular reamer surgical tool along the longitudinal axis,
wherein the guide body has a slot defined therein extending orthogonally to the longitudinal axis, and the guide housing has a flange extending from an end securable to the guide body, the flange being sized to be received in the slot of the guide body to secure the guide housing to the guide body.

* * * * *